United States Patent [19]

Nagy

[11] 4,360,361

[45] Nov. 23, 1982

[54] COAL GASIFICATION APPARATUS

[75] Inventor: Charles K. Nagy, Monaca, Pa.

[73] Assignee: United States Department of Energy, Washington, D.C.

[21] Appl. No.: 257,088

[22] Filed: Apr. 24, 1981

[51] Int. Cl.³ ............................................. C10J 3/68
[52] U.S. Cl. ...................................... 48/77; 165/169; 422/203
[58] Field of Search ...................... 48/210, 77, 63, 64, 48/76; 422/203; 165/168, 169, 157

[56] References Cited

U.S. PATENT DOCUMENTS

| | | | |
|---|---|---|---|
| 865,727 | 9/1907 | Queneau | 48/63 |
| 1,738,620 | 12/1979 | Umpleby | 422/203 |
| 1,849,279 | 3/1932 | Cezanne | 48/76 |
| 2,072,357 | 3/1937 | Carson | 48/64 |
| 2,175,610 | 10/1939 | Linder | 48/76 |
| 2,761,772 | 9/1956 | Atwell | 48/76 |
| 4,142,867 | 3/1979 | Kiener | 48/76 |

Primary Examiner—S. Leon Bashore, Jr.
Assistant Examiner—Michael L. Goldman
Attorney, Agent, or Firm—Edwin D. Grant; Stephen D. Hamel; Richard G. Besha

[57] ABSTRACT

Coal hydrogenation vessel has hydrogen heating passages extending vertically through its wall and opening into its interior.

4 Claims, 1 Drawing Figure

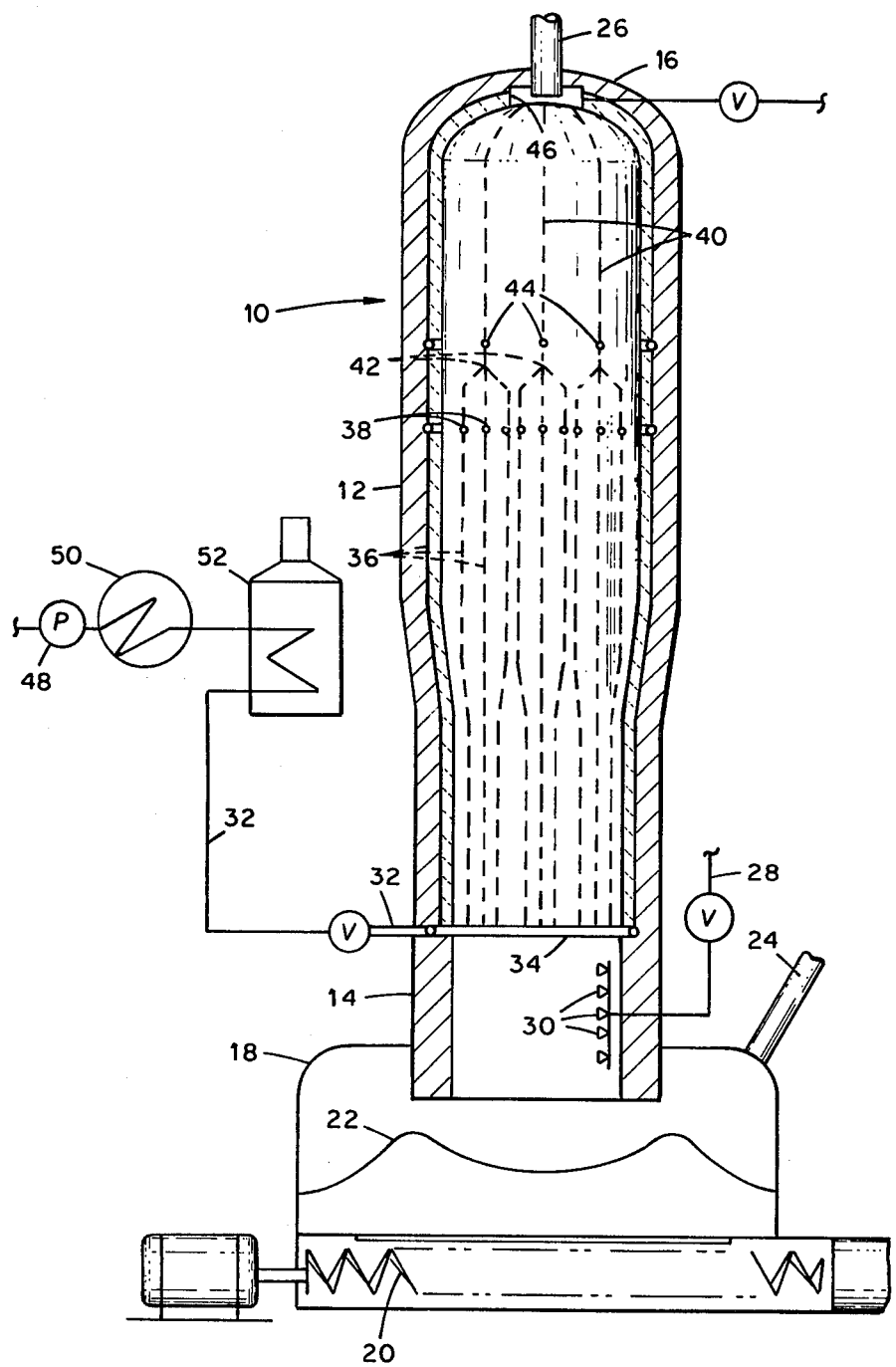

COAL GASIFICATION APPARATUS

BACKGROUND OF THE INVENTION

This invention, which results from a contract with the United States Department of Energy, relates to coal hydrogenation.

Commercial processes for the production of synthetic gas involve the reaction of finely divided coal with hydrogen and steam at elevated pressure and at temperatures which can exceed 2500° F. To achieve the desired reaction conditions, the hydrogen required for these processes must be preheated to about 2000° F. A large amount of energy is, of course, used by the heaters which raise hydrogen to the required 2000° F. temperature.

SUMMARY OF THE INVENTION

It is an object of this invention to utilize the heat generated by a coal hydrogenation reaction to provide a portion of the energy required for raising the temperature of hydrogen introduced into the reaction vessel.

Another object of the invention is to arrange flow passages in the wall of a coal hydrogenation reaction vessel so that hydrogen passed through the passages is effectively heated by energy transmitted into the wall by the hydrogenation reaction occurring in the vessel.

These objects are attained by a preferred apparatus embodiment of the invention comprising:

a reaction vessel formed with (1) a vertically disposed tubular casing having a cover attached to the upper end thereof, (2) a coal inlet in said cover, (3) a plurality of flow passages extending vertically through the wall of said casing and circumferentially spaced apart from one another, (4) a plurality of feed holes respectively communicating with said flow passages and the interior of said vessel; and means for forcing hydrogen through said flow passages and said feed holes into said vessel.

DESCRIPTION OF THE DRAWING

The single FIGURE is a diagrammatic, cross-sectional representation of the preferred apparatus embodiment of the invention, taken along a plane including the longitudinal axis of the hydrogenation reaction vessel thereof.

DETAILED DESCRIPTION OF THE PREFERRED EMBODIMENT

In the drawing, reference number 10 generally designates a coal hydro-gasifier reaction vessel in which hydrogen and steam are contacted with pulverized coal to produce methane. Vessel 10 consists of a vertically disposed, tubular casing 12, the lower portion 14 of which has a reduced diameter and the upper end of which is closed by a cover 16. The lower end of casing 12 is connected to, and communicates with the interior of, a chamber 18 containing an auger tube 20 for discharging the mixture 22 of unreacted coal particles and ash material accumulated therein. Methane passes from chamber 18 through a conduit 24.

Pulverized coal enters vessel 10 via an inlet conduit 26 which extends through cover 16 in coaxial relation with casing 12, and preheated water is forced through a conduit 28 to a plurality of nozzles 30 located in the lower portion of the casing, this water flashing to steam as it issues from the nozzles.

The wall of vessel 10 is preferably formed of an inner refractory lining, a layer of insulation surrounding the inner lining, and an outer metal shell. A feed conduit 32 delivers hydrogen to an inlet manifold passage 34 which is formed in the inner lining of the wall of vessel 10 and which extends completely therearound. Spaced apart from one another circumferentially of vessel 10 are a plurality of flow passages 36 which are also formed in the inner lining of the vessel and which connect at their lower ends with inlet manifold passage 34. Located at the middle portion of vessel 10 is a first set of feed holes 38 each of which extends from a respective one of the flow passages 36 to the inner surface of the vessel, the longitudinal axes of these holes lying in a plane disposed perpendicular to the longitudinal axis of said vessel. Sets of three flow passages 36 are joined together above feed holes, and a continuation flow passage 40 extends upward from the junction 42 of the united flow passages of each of these sets. A second set of feed holes 44 is located above junctions 42, and each of these holes extends from a respective one of the flow passages 40 to the inner surface of vessel 10. The longitudinal axes of feed holes 44 also lie in a plane disposed perpendicular to the longitudinal axis of said vessel. Flow passages 40 extend upward to and through cover 16 to the side surface 46 of a recess formed therein.

Hydrogen is forced through the above-described system of flow passages 36, 40 by a pump 48 connected to feed conduit 32, this hydrogen being heated by a heat exchanger 50 and a gas fueled furnace 52 located between the pump and vessel 10. The temperature of the hydrogen entering inlet manifold passage 34 and flowing upward through flow passages 36 and 42 is further raised by heat energy transmitted into the wall of casing 12 and cover 16 from the hydrogenation reaction occurring in vessel 10. Thus only a portion of the total amount of energy required to heat the hydrogen feed to its hydrogenating temperature is supplied by heat exchanger 50 and furnace 52, and the remainder of this energy is supplied by the hydrogenation reaction itself. The amount of energy saved by the disclosed coal hydrogenation apparatus and process will vary depending upon the operating conditions involved therewith. However, in some coal gasification apparatus, the invention will permit final preheating of hydrogenation from about 1600° F. to 200 ° F. in flow passages 36 and 40, thus conserving the fuel normally required for this heating.

What is claimed is:

1. Coal hydrogenation apparatus comprising:
a reaction vessel having (1) a vertically disposed tubular wall with an upper end and a lower end, the inner surface of said tubular wall circumscribing a reaction chamber, (2) a cover attached to the upper end of said tubular wall, (3) a coal inlet in said cover, (4) a plurality of flow passages located in direct heat transfer relation within said tubular wall and extending vertically from the lower portion thereof toward said cover, said flow passages being circumferentially spaced apart from one another in said tubular wall, and (5) a plurality of feed holes located within said tubular wall and respectively communicating with said flow passages and the interior of said reaction chamber, said plurality of feed holes comprising: a plurality of first feed holes equidistant from said cover; and a plurality of second feed holes equidistant from said cover and located between said cover and said first feed holes, wherein a plurality of said flow passages are joined together within said tubular wall between said first feed holes and said second feed holes; and means for forcing hydrogen through said flow passages and said feed holes into the interior of said vessel.

2. The apparatus of claim 1 wherein at least some of said flow passages extends into said cover and communciate with the interior of said vessel adjacent said coal inlet.

3. The apparatus of claim 1 including an inlet manifold passage located within the lower portion of said tubular wall and communicating with said flow passages.

4. The apparatus of claim 3 including means for heating said hydrogen before it is forced through said flow passages.

* * * * *